United States Patent [19]

Balli et al.

[11] Patent Number: 4,503,227
[45] Date of Patent: Mar. 5, 1985

[54] CHROMOGENIC DIHYDROQUINAZOLINES

[75] Inventors: Heinz Balli, Riehen; Sigmund Gunzenhauser, Arlesheim; Ian J. Fletcher, Magden; Davor Bedekovic, Therwil, all of Switzerland

[73] Assignee: Ciba-Geigy Corporation, Ardsley, N.Y.

[21] Appl. No.: 485,916

[22] Filed: Apr. 18, 1983

[30] Foreign Application Priority Data

Apr. 22, 1982 [CH] Switzerland .................. 2447/82

[51] Int. Cl.³ .................. C07D 403/14; C07D 403/10; C07D 403/04; C07D 239/74
[52] U.S. Cl. .................. 544/246; 544/80; 544/115; 544/247
[58] Field of Search .................. 544/80, 115, 247, 246

[56] References Cited

U.S. PATENT DOCUMENTS 4,183,932  1/1980  Yamamoto et al. .................. 544/247

Primary Examiner—John M. Ford
Attorney, Agent, or Firm—Edward M. Roberts

[57] ABSTRACT

The invention relates to chromogenic dihydroquinazolines of the general formula

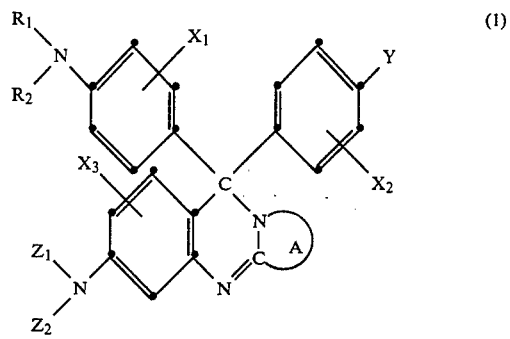

wherein the ring A is a monocyclic or polycyclic, unsubstituted or substituted heterocyclic radical which may contain further heteroatoms as ring members, each of $X_1$, $X_2$ and Y independently of one another is hydrogen, halogen, lower alkyl, lower alkanoylamino, or a group of the formula

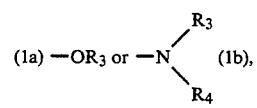

$X_3$ is hydrogen, halogen, lower alkyl or lower alkoxy;

each of $R_1$, $R_2$, $R_3$, $R_4$, $Z_1$ and $Z_2$ independently of one another is $C_1$–$C_{12}$ alkyl which is unsubstituted or substituted by halogen, hydroxyl, cyano or lower alkoxy, or is cycloalkyl, phenyl, or phenyl or benzyl each substituted by halogen, nitro, lower alkyl or lower alkoxy, and the radicals R may also be hydrogen; or each pair of substituents ($R_1$ and $R_2$), ($R_3$ and $R_4$) and ($Z_1$ and $Z_2$) independently of one another, together with the nitrogen atom to which said pair is attached, is a 5- or 6-membered heterocyclic radical.

These compounds are particularly suitable for use as color formers in pressure-sensitive or heat-sensitive recording materials and produce lightfast blue, greenish blue or green colorations.

6 Claims, No Drawings

CHROMOGENIC DIHYDROQUINAZOLINES

The present invention relates to chromogenic dihydroquinazolines, to a process for their preparation, and to the use of these compounds as colour formers in pressure-sensitive or heat-sensitive recording materials.

The dihydroquinazolines of this invention have the general formula

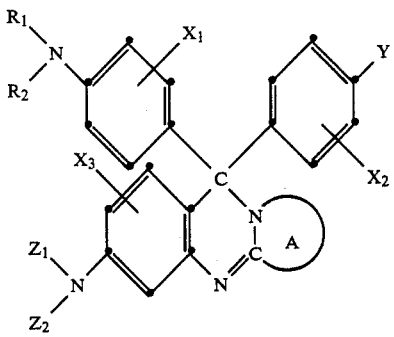

wherein
the ring A is a monocyclic or polycyclic, unsubstituted or substituted heterocyclic radical which may contain further heteroatoms as ring members, each of $X_1$, $X_2$ and Y independently of one another is hydrogen, halogen, lower alkyl, lower alkanoylamino, or a group of the formula

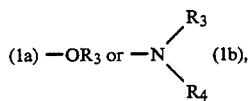

$X_3$ is hydrogen, halogen, lower alkyl or lower alkoxy; each of $R_1$, $R_2$, $R_3$, $R_4$, $Z_1$ and $Z_2$ independently of one another is $C_1$-$C_{12}$alkyl which is unsubstituted or substituted by halogen, hydroxyl, cyano or lower alkoxy, or is cycloalkyl, phenyl, benzyl, or phenyl or benzyl each substituted by halogen, nitro, lower alkyl or lower alkoxy, and the radicals R may also be hydrogen; or
each pair of substituents ($R_1$ and $R_2$), ($R_3$ and $R_4$) and ($Z_1$ and $Z_2$) independently of one another, together with the nitrogen atom to which said pair is attached, is a 5- or 6-membered, preferably saturated, heterocyclic radical.

Y is preferably a group of the formula (1b)

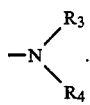

The groups of the formulae —$NR_1R_2$ and —$NR_3R_4$ may differ from each other or they are preferably identical. $X_1$ and $X_2$ are preferably also identical.

In the definitions of the radicals of the dihydroquinazolines, the term "lower" qualifying alkyl and alkoxy groups will normally be understood to denote groups which contain 1 to 5, preferably 1 to 3, carbon atoms. Examples of lower alkyl groups are methyl, ethyl, n-propyl, isopropyl, n-butyl, sec-butyl or amyl; and examples of lower alkoxy groups are methoxy, ethoxy or isopropoxy.

Lower alkanoylamino usually contains 2 to 5 carbon atoms and is e.g. acetylamino, propionylamino or butyrylamino. Halogen in connection with all substituents referred to above and hereinafter is e.g. fluorine, bromine or, preferably, chlorine.

$R_1$, $R_2$, $R_3$, $R_4$, $Z_1$ and $Z_2$ as alkyl groups may be straight chain or branched alkyl groups, e.g. methyl, ethyl, n-propyl, isopropyl, n-butyl, sec-butyl, amyl, n-hexyl, 2-ethylhexyl, n-octyl, isooctyl or n-dodecyl.

$R_1$, $R_2$, $R_3$, $R_4$, $Z_1$ and $Z_2$ as substituted alkyl groups are in particular cyanoalkyl, haloalkyl, hydroxyalkyl or alkoxyalkyl, each containing preferably a total of 2 to 4 carbon atoms, e.g. $\beta$-cyanoethyl, $\beta$-chloroethyl, $\beta$-hydroxyethyl, $\beta$-methoxyethyl or $\beta$-ethoxyethyl.

$R_1$, $R_2$, $R_3$, $R_4$, $Z_1$ and $Z_2$ as cycloalkyl may be cyclopentyl or, preferably, cyclohexyl.

Preferred substituents in the benzyl moiety and in the phenyl moiety of the radicals R and Z are e.g. halogens, nitro, methyl or methoxy. Examples of such araliphatic and aromatic radicals are p-methylbenzyl, o- or p-chlorobenzyl, o- or p-nitrobenzyl, o- or p-tolyl, xylyl, o-, m- or p-chlorophenyl, o- or p-nitrophenyl, or o- or p-methoxyphenyl.

A heterocyclic radical represented by each pair of substituents ($R_1$ and $R_2$), ($R_3$ and $R_4$), and ($Z_1$ and $Z_2$) together with the nitrogen atoms to which said pair is attached, is e.g. pyrrolidino, piperidino, pipecolino, morpholino, thiomorpholino or piperazino.

The substituents $R_1$, $R_2$, $R_3$, $R_4$, $Z_1$ and $Z_2$ are preferably benzyl, lower alkyl or cyano-lower alkyl, e.g. $\beta$-cyanoethyl.

$X_1$, $X_2$ and $X_3$ are preferably each hydrogen. However, they may also with advantage be methyl, methoxy, ethoxy or chlorine, each preferably in ortho-position to the central carbon bond. $X_1$ and $X_2$ may also with advantage be acetylamino.

The heterocyclic ring A may be monocyclic or polycyclic and may contain 5 to 15, preferably 5 to 10 ring members, and, depending on the system, may contain a total of 1 to 3, preferably 1 or 2, hetero atoms as ring members.

The ring A is preferably an N-heterocyclic ring which is derived from a 5- or 6-membered heterocyclic system of aromatic character. In addition to the nitrogen atom, this heterocyclic ring system may contain oxygen, sulfur, selenium or further nitrogen atoms. For example, the ring A may be derived from pyrazole, imidazole, oxazole, selenazole, thiazole, isothiazole, triazole, thiadiazole, pyridine, pyrimidine, pyrazine or triazine, each of which may be unsubstituted or substituted.

A is preferably a bicyclic heterocyclic ring system which contains a benzene ring fused to the heterocyclic ring and may be derived e.g. from an unsubstituted or substituted indole, indazole, benzimidazole, benzothiazole, benzisothiazole, benzoxazole, benzoselenazole, quinoline, isoquinoline, quinoxaline, quinazoline, phthalazine or cinnoline.

If desired, the heterocyclic ring A may also be a tricyclic radical in which the nitrogen ring is fused to a naphthalene nucleus, e.g. in benz[c,d]indole.

The monocyclic, bicyclic or tricyclic radicals A may be substituted by one or more identical or different radicals selected from the group consisting of e.g. halogen, cyano, nitro, hydroxyl, lower alkyl, lower alkoxy, lower alkylcarbonyl, lower carbalkoxy, lower alkylamino, di-lower alkylamino or arylamino, e.g. phenylamino, chlorophenylamino or tolylamino.

The heterocyclic radicals may also originate from non-aromatic compounds. Examples of such substituents are the partially saturated heterocyclic radicals corresponding to the above aromatic heterocyclic ring systems, and are e.g. indoline or tetrahydroquinoline radicals, or heterocyclic rings which contain keto groups, e.g. 3H-indole-3-one, which may also be substituted e.g. by halogen, lower alkyl, cyclohexyl or benzyl.

Useful colour formers of this invention are dihydroquinazolines of the formula

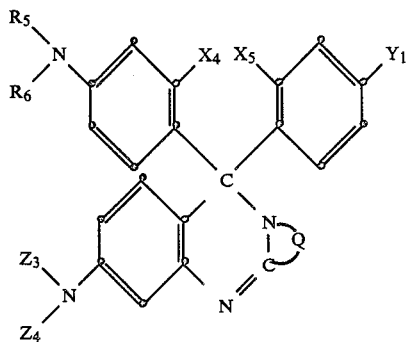
(2)

wherein
$Y_1$ is hydrogen, $-OR_7$ or

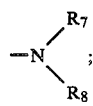

each of $X_4$ and $X_5$ independently of the other is hydrogen, halogen, methyl, methoxy, ethoxy or acetylamino; each of
$R_5$, $R_6$, $R_7$, $R_8$, $Z_3$ and $Z_4$ independently of one another is lower alkyl, cyanoethyl, benzyl or phenyl, or each pair of substituents ($R_5$ and $R_6$), ($R_7$ and $R_8$) and ($Z_3$ and $Z_4$) independently of one another, together with the nitrogen atom to which said pair is attached, is pyrrolidino, piperidino or morpholino; and
Q is the member required to complete a ring system of the formula

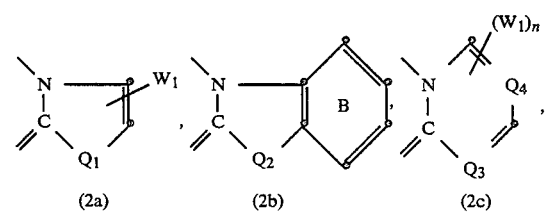
(2a) (2b) (2c)

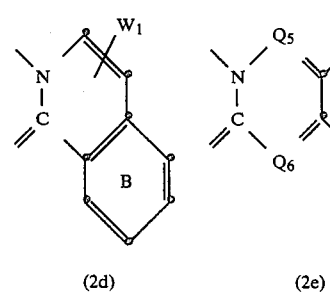
(2d) (2e)

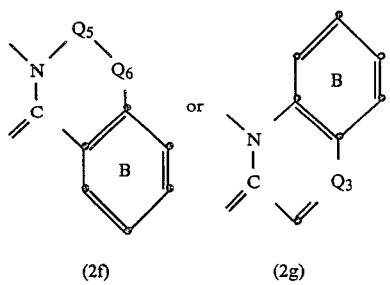
(2f) (2g)

wherein
$Q_1$ is oxygen, sulfur, selenium or

$Q_2$ is oxygen, sulfur, selenium,

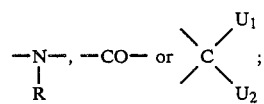

each of $Q_3$ and $Q_4$ independently of the other is

or $-N=$;
one of $Q_5$ and $Q_6$ is

and the other is $-N=$,
T is hydrogen or lower alkyl; each of
$U_1$ and $U_2$ independently of the other is lower alkyl, cyclohexyl, benzyl, or taken together they are alkylene; each of
$W_1$ and $W_2$ independently of the other is hydrogen, halogen, lower alkyl, lower alkoxy, lower carbalkoxy, mono- or di-lower alkylamino, pyrrolidino, piperidino, pipecolino, morpholino or arylamino e.g. phenylamino, and n is 1 or 2, and
the rings B and D are unsubstituted or substituted by halogen, lower alkyl, lower alkoxy or lower carbalkoxy.

Among these compounds of the formula (2), particularly preferred compounds are those in which $Y_1$ is the group of the formula $-NR_7R_8$ and Q completes the radical of the formula (2a), (2c), (2f) or, preferably (2b).

Preferred colour formers are dihydroquinazolines of the formula

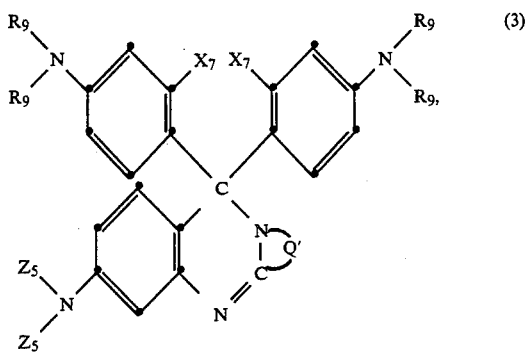

wherein each of $Z_5$ and $R_9$ independently of the other is lower alkyl, preferably methyl or ethyl, $X_7$ is methoxy or ethoxy or, preferably, hydrogen, and

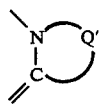

is a heterocyclic ring system of the formula

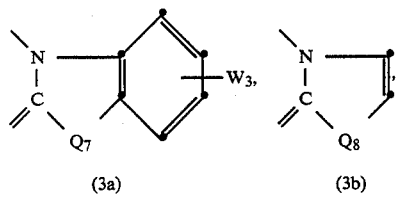

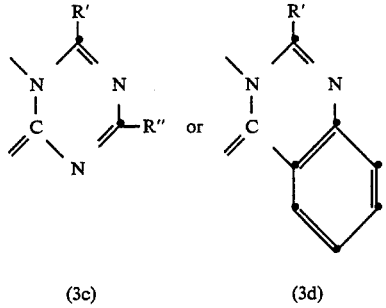

wherein $Q_7$ is

—O—, —S—, —Se—, —CO or =C(CH$_3$)$_2$, T is hydrogen or lower alkyl, $W_3$ is hydrogen, halogen, methyl, methoxy or acetoxy, $Q_8$ is oxygen or sulfur, and each of R' and R" independently of the other is hydrogen, lower alkyl, preferably methyl, lower alkoxy such as methoxy, or is di-lower alkylamino, pyrrolidino, piperidino or morpholino.

Among the dihydroquinazolines of the formula (3), those compounds are particularly preferred in which Q' completes the heterocyclic ring system of the formula (3a). Preferred dihydroquinazolines of the formula (3) are furthermore those in which $R_9$ and $Z_5$ are methyl or ethyl, $X_7$ is hydrogen, and

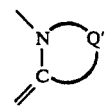

is a ring system of the formula (3a) wherein $Q_7$ is sulfur and $W_3$ is hydrogen.

The dihydroquinazolines of the formula (1) are obtained by reacting an m-phenylenediamine compound which is substituted by a heterocyclic radical and has the formula

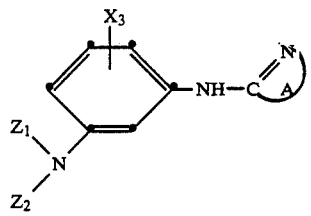

with a keto compound of the formula

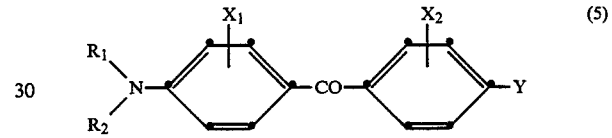

or with a carbonol compound of the formula

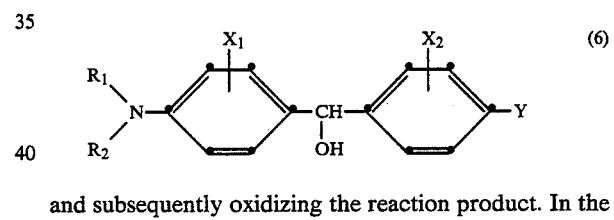

and subsequently oxidizing the reaction product. In the formulae (4), (5) and (6) above, A, $R_1$, $R_2$, $X_1$, $X_2$, $X_3$, Y, $Z_1$ and $Z_2$ have the given meanings.

The reaction with the keto compound of the formula (5) is preferably carried out by reacting the reaction components in the presence of an acid condensing agent, e.g. sulfuric acid, oleum, phosphorus pentoxide or, preferably, an acid halide.

Suitable acid halides are acid bromides or, preferably, acid chlorides, of phosphorus acid or sulfurous acid, of phosphoric acid, sulfuric acid, carbonic acid or oxalic acid. It is advantageous to use oxalyl chloride, oxalyl bromide, thionyl chloride, sulfuryl chloride, phosphorus trichloride, phosphorus tribromide or, preferably, phosgene or, most preferably, phosphoroxy trichloride.

The reaction of the compound of the formula (4) with the keto compound of the formula (5) may be carried out in the temperature range from 20° to 120° C. It is advantageous to maintain anhydrous conditions. An excess of the acid halide employed may be used as reaction medium, but an inert solvent can also be added.

Examples of suitable solvents are: cycloaliphatic or aromatic hydrocarbons such as cyclohexane, benzene, toluene or xylene; chlorinated hydrocarbons such as chloroform, carbon tetrachloride, ethylene chloride or chlorobenzenes; ethers such as dioxan, diethyl ether, glycol dimethyl ether or tetrahydrofuran.

The concentration of the reactants is not critical; however, it is advantageous to use one molar equivalent of each of the reactants. The process is ordinarily carried out by adding all the reactants, i.e. the compound of formula (4), the compound of formula (5) and the acid halide, simultaneously. However, it is also possible first to react the compound of formula (4) and the acid halide and then to add the compound of formula (5). The final product of the formula (1) is isolated in conventional manner, e.g. by pouring the reaction mixture into ice/water, if desired while neutralising the acid with an alkali, e.g. an alkali metal hydroxide or alkali metal carbonate, removing the precipitate by filtration and washing and drying it, and also, if appropriate, by chromatography or recrystallisation of the product. Liquid final products can be obtained by extraction with suitable organic solvents and purified by distillation.

The condensation of the compound of formula (4) with the compound of formula (6) is conveniently carried out in an organic solvent, preferably in a lower aliphatic alcohol, e.g. methanol, ethanol or isopropanol, or in an ether such as tetrahydrofuran and preferably in the presence of an acid catalyst. The reaction may be carried out at room temperature (20° to 25° C.), but elevated temperature, preferably in the range from 40° to 100° C., is advantageous. Examples of suitable acid catalysts are lower aliphatic carboxylic acids such as formic acid or acetic acid, and inorganic acids such as hydrochloric acid, sulfuric acid, phosphoric acid or perchloric acid.

The reaction of the compound of formula (4) with the compound of formula (6), accompanied by dehydration, gives a reaction product of the formula

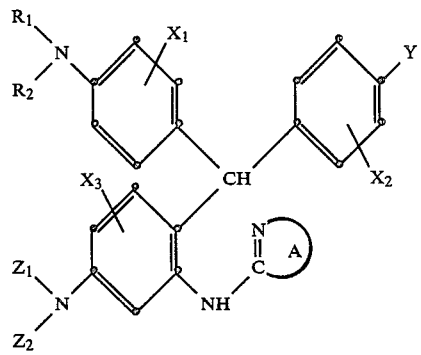

wherein A, $R_1$, $R_2$, $X_1$, $X_2$, $X_3$, Y, $Z_1$ and $Z_2$ have the given meanings.

The reaction product of the formula (7) may, if desired, be isolated.

The oxidation of the reaction product of the formula (7) to give the dihydroquinazoline of the formula (1) is carried out with an oxidising agent, e.g. a chromate, bichromate, chlorate, chlorite, peroxide, manganese dioxide, lead dioxide, chlorine, bromine, molecular oxygen, air, a perborate, permanganate, hydrogen peroxide, chloranil or potassium hexacyanoferrate(III).

The reaction is conveniently carried out in the presence of an organic solvent which does not participate in the oxidation. Suitable solvents are likewise lower aliphatic alcohols such as ethanol, isopropanol, ethylene glycol monomethyl or monoethyl ether, or lower aliphatic ketones such as acetone, methylethyl ketone or methyl isobutyl ketone, aromatic hydrocarbons such as benzene or toluene, as well as N-methylpyrrolidone, γ-butyrolactone, acetonitrile or dimethylsulfoxide.

The oxidation temperature normally depends on the oxidising agent and, in particular, on the boiling point of the solvent employed. It is conveniently in the range from 20° to 150° C., preferably from 20° to 100° C.

The starting materials of the formula (4) may be prepared in a manner known per se. A preferred process for obtaining the starting materials of the formula (4) consists in reacting a meta-phenylenediamine of the formula

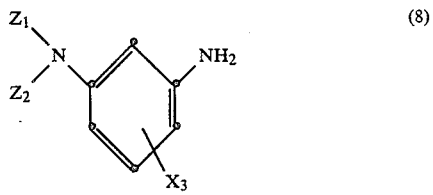

with a heterocyclic compound of the formula

wherein A, $Z_1$, $Z_2$ and $X_3$ have the given meanings and Hal is iodine, bromine, fluorine or, preferably, chlorine.

Examples of heterocyclic compounds which may be used as starting materials of the formula (9) are: 2-chlorothiazole, 2-chloropyridine, 2-chloropyrimidine, 2,4-dichloropyrimidine, cyanuric chloride, cyanuric bromide, cyanuric fluoride, 2-chlorobenzothiazole, 2-chlorobenzoselenazole, 2-chloroquinoline, 2-chloroisatine, 1-chlorophthalazine, 3- or 4-chlorocinnoline, 2-chloro-3,3-dimethylindolenine, 2-chloroquinazoline and 2-chloroquinoxaline.

Preferred starting materials of the formulae (5) and (6) are 4,4-bis(dimethylamino)benzophenone (Michler's ketone) and 4,4'-bis-(dimethylamino)benzhydrol (Michler's hydrol).

The dihydroquinazolines of the formulae (1) to (3) are normally colourless or, at most, faintly coloured. When these colour formers are brought into contact preferably with an acid developer, e.g. an electron acceptor, they produce intense blue, greenish blue or green shades of excellent fastness to sublimation and light. They are therefore also very useful when mixed with one or more other known colour formers, for example 3,3-(bis-aminophenyl)-phthalides, 3,3-(bis-indolyl)-phthalides, 3-aminofluoranes, 2,6-diaminofluoranes, leucoauramines, spiropyranes, spirodipyranes, chromenoindoles, phenoxazines, phenothiazines, carbazolylmethanes or other triarylmethaneleuco dyes, to give blue, navy blue, grey or black colorations.

The dihydroquinazolines of the formulae (1) to (3) exhibit both on phenolic substrates and especially on activated clays an improved colour intensity and lightfastness. They are suitable in particular as rapidly developing colour formers for use in a heat-sensitive or especially in a pressure-sensitive recording material which can also be a copying material.

A pressure-sensitive material consists, for example, of at least one pair of sheets which contain at least one colour former of the formulae (1) to (3) dissolved in an organic solvent, and a solid electron acceptor as developer.

Typical examples of such developers are activated clays such as attapulgite, acid clay, bentonite, montmorillonite, activated clay, e.g. acid-activated bentonite or montmorillonite, and also zeolith, halloysite, silica, alumina, aluminium sulfate, aluminium phosphate, zinc chloride, activated kaolin or any clay. Preferred developers are acidic organic compounds, for example unsubstituted or ring-substituted phenols, salicylic acid or salicylates and their metal salts, or an acidic polymer, for example a phenolic polymer, an alkylphenolacetylene resin, a maleic acid/rosin resin or a partially or completely hydrolysed polymer of maleic acid and styrene, ethylene or vinyl methyl ether, or carboxypolymethylene. Mixtures of these polymers can also be used. Particularly preferred developers are zinc salicylates or the condensation products of p-substituted phenols with formaldehyde. These latter may also contain zinc.

The developers may also be used with other basically inert or almost inert pigments. Examples of such pigments are: talcum, titanium dioxide, zinc oxide, chalk, clays such as kaolin, as well as organic pigments, e.g. urea/formaldehyde or melamine/formaldehyde condensates.

The colour former effects a coloured marking at those points where it comes into contact with the electron acceptor. In order to prevent the colour formers contained in the pressure-sensitive recording material from becoming active prematurely, they are usually separated from the electron acceptor. This separation can conveniently be accomplished by incorporating the colour formers in foamlike, spongelike or honeycomblike structures. The colour formers are preferably encapsulated in microcapsules, which as a rule can be ruptured by pressure.

When the capsules are ruptured by pressure, for example with a pencil, the colour former solution is transferred to an adjacent sheet which is coated with an electron acceptor and a coloured area is thus produced. This colour results from the dye which is formed and which is absorbed in the visible range of the electromagnetic spectrum.

The colour formers are encapsulated preferably in the form of solutions in organic solvents. Examples of suitable solvents are preferably non-volatile solvents, for example a polyhalogenated paraffin, such as chloroparaffin, or a polyhalogenated diphenyl, such as monochlorodiphenyl or trichlorodiphenyl, and also tricresyl phosphate, di-n-butyl phthalate, dioctyl phthalate, trichlorobenzene, trichloroethylphosphate, an aromatic ether such as benzylphenyl ether, a hydrocarbon oil such as paraffin or kerosene, an alkylated (e.g. with isopropyl, isobutyl, sec- or tert-butyl) derivative of diphenyl, naphthalene or triphenyl; dibenzyl toluene, terphenyl, partially hydrogenated terphenyl, a benzylated xylene, or other chlorinated or hydrogenated, condensed aromatic hydrocarbons. Mixtures of different solvents, especially mixtures of paraffin oils or kerosene and diisopropylnaphthalene or partially hydrogenated terphenyl, are often used in order to obtain an optimum solubility for the colour formation, a rapid and intense coloration, and a viscosity which is advantageous for the microencapsulation.

The capsule walls can be formed evenly around the droplets of the colour former solution by coacervation; and the encapsulating material can consist of gelatin and gum arabic, as described e.g. in U.S. Pat. No. 2,800,457. The capsules can also be formed preferably from an aminoplast or a modified aminoplast by polycondensation, as described in British patent specification Nos. 989,264, 1,156,725, 1,301,052 and 1,355,124. Also suitable are microcapsules which are formed by interfacial polymerisation, e.g. capsules formed from polyester, polycarbonate, polysulfonamide, polysulfonate, but in particular from polyamide or polyurethane.

The microcapsules containing the colour formers of the formulae (1) to (3) can be used for the production of a wide variety of known kinds of pressure-sensitive copying material. The various systems differ substantially from one another in the arrangement of the capsules, of the colour reactants, i.e. the developers, and/or of the support. A preferred arrangement is that in which the encapsulated colour former is in the form of a layer on the back of a transfer sheet and the developer is in the form of a layer on the face of a receiver sheet. Another arrangement of the components is that wherein the microcapsules which contain the colour former, and the developer, are in or on the same sheet, in the form of one or more individual layers, or are present in the paper pulp.

The capsules are preferably secured to the support by means of a suitable adhesive. As paper is the preferred support, these adhesives are principally paper-coating agents, for example gum arabic, polyvinyl alcohol, hydroxymethyl cellulose, casein, methyl cellulose, dextrin, starch or starch derivatives or polymer latices. These latter are e.g. butadiene/styrene copolymers or acrylic homopolymers or copolymers.

The paper employed comprises not only normal paper made from cellulose fibres, but also paper in which the cellulose fibres are replaced (partially or completely) by synthetic polymers.

The compounds of the formulae (1) to (3) can also be employed as colour formers in a thermoreactive recording material. This recording material usually contains at least one carrier, one colour former, one electron acceptor and, optionally, also a binder. Thermoreactive recording systems comprise, for example, heat-sensitive recording or copying materials or papers. These systems are used e.g. for recording information, for example in electronic computers, teleprinters or telewriters, or in recording and measuring instruments, e.g. electrocardiographs. The image (mark) formation can also be effected manually with a heated pen. Laser beams can also be used to produce heat-induced marks.

The thermoreactive recording material can be composed such that the colour former is dispersed or dissolved in one binder layer and the developer is dissolved or dispersed in the binder in a second layer. Another possibility consists in dispersing both the colour former and the developer in one layer. Be means of heat the binder is softened at specific areas and the colour former comes into contact with the developer (electron acceptor) at those points where heat is applied and the desired colour develops at once.

Suitable developers are the same electron acceptors as are used in pressure-sensitive papers. Examples of developers are the clays already mentioned and especially phenolic resins, or also the phenolic compounds described e.g. in German Offenlegungsschrift No. 1 251 348, for example 4-tert-butylphenol, 4-phenylphenol, 4-hydroxydiphenyl ether, α-naphthol, β-naphthol, 4-hydroxymethylbenzoate, 4-hydroxyacetophenone, 2,2'-dihydroxydiphenyl, 4,4-isopropylidenediphenol, 4,4'- isopropylidene-bis-(2-methylphenol), 4,4'-bis-(hydroxyphenyl) valeric acid, 2,2'-methylene-bis-(4-phenylphenol), hydroquinone, pyrogallol, phloroglucinol, p-, m- and o-hydroxybenzoic acid, gallic acid, 1-hydroxy-2-naphthoic acid, as well as boric acid or organic, preferably aliphatic, dicarboxylic acids, for example tartaric acid, oxalic acid, maleic acid, citric acid, citraconic acid or succinic acid.

Fusible, film-forming binders are preferably used for the manufacture of the thermoreactive recording material these binders are normally water-soluble, whereas the dihydroquinazolines and the developer are sparingly soluble or insoluble in water. The binder should be able to disperse and fix the colour former and the developer at room temperature.

By applying heat the binder softens or melts, so that the colour former comes in contact with the developer and a colour is able to form. Examples of binders which are soluble, or at least swellable, in water are e.g. hydrophilic polymers, for example polyvinyl alcohol, polyacrylic acid, hydroxyethylcellulose, methyl cellulose, carboxymethylcellulose, polyacrylamide, polyvinyl pyrrolidone, gelatin and starch.

If the colour former and the developer are in two separate layers, it is possible to use water-soluble binders, i.e. binders which are soluble in non-polar or only weakly polar solvents, for example natural rubber, synthetic rubber, chlorinated rubber, alkyd resins, polystyrene, styrene/butadiene copolymers, polymethylacrylates, ethyl cellulose, nitrocellulose and polyvinyl carbazole. The preferred arrangement, however, is that in which the colour former and the developer are contained in one layer in a water-soluble binder.

The thermoreactive coatings may contain further ingredients. To improve the degree of whiteness, to facilitate the printing of papers, and to prevent the heated pen from sticking, the coatings may contain e.g. talcum, titanium dioxide, zinc oxide, aluminium hydroxide, calcium carbonate (e.g. chalk), clays or also organic pigments, for example urea/formaldehyde polymers. In order to effect the colour formation only within a limited temperature range, it is possible to add substances such as urea, thiourea, diphenyl thiourea, acetamide, acetanilide, stearyl amide, phthalic anhydride, metal stearates, phthalonitrile or other appropriate fusible products which induce the simultaneous melting of the colour former and the developer. Thermographic recording materials preferably contain waxes, e.g. carnauba wax, montan wax, paraffin wax or polyethylene wax.

The invention is illustrated by the following Examples, in which percentages are by weight, unless otherwise indicated.

EXAMPLE 1

2-Dimethylamino-5,5-bis-(4-dimethylaminophenyl)-5,6-dihydroquinazolino[2,3-b]benzothiazoline.

A mixture of 1 mmole of 4,4'-bis(dimethylamino)benzophenone (Michler's ketone) and 1 mmole of (2-benzothiazolyl)-3-diethylaminophenylamine in 10 ml of phosporoxy trichloride is heated to reflux for 1½ to 2 hours. The reaction mixture is poured on ice, washed with a small amount of methanol, made alkaline with concentrated ammonia and stirred for 1 hour at room temperature. The precipitate is isolated by filtration and taken up in dichloromethane or toluene. The solution is dried over anhydrous sodium sulfate and chromatographed over 70 g of silica gel with a 10:1 to 5:1 mixture of toluene/ethyl acetate. The main fraction is recrystallised from methanol, affording 320 mg (58% of theory) of a compound of the formula

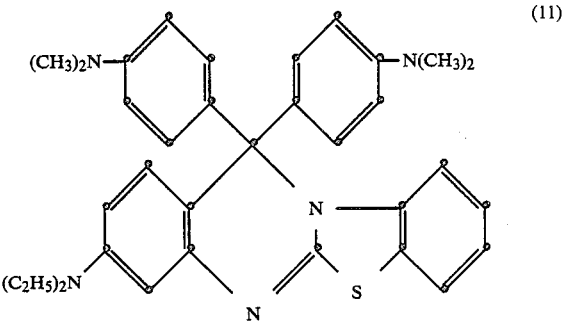

in the form of white crystals which melt at 141°–142° C. This colour former develops an intense blue colour on acid clay.

The (2-benzothiazolyl)-3-diethylaminophenylamine used as starting material in this Example is prepared as follows:

10 mmoles of hydrochloric acid (corresponding to 1 ml of 32.5% hydrochloric acid) are added to 10 mmoles of N,N-diethyl-m-phenylene-diamine and 10 mmoles of 2-chlorobenzothiazole, and the reaction mixture is heated under strong reflux for 15 hours in 100 ml of a 1:9 mixture of ethanol/water. With stirring, the hot solution is adjusted to pH 7–8 with aqueous 2N sodium hydroxide solution. The precipitate is isolated from the cooled solution and dried, affording 2.64 g of a crude product which is crystallised from ethanol to give 2.43 g (82% of theory) of a compound of the formula

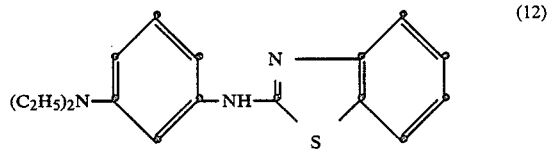

which has a melting point of 134°–135° C.

EXAMPLE 2

13.5 g of 4,4'-bis(dimethylamino)benzhydrol and 14.0 g of (2-benzthiazolyl)-3-diethylaminophenylamine are stirred under reflux for 5 hours in 150 ml of ethanol in the presence of 1.5 ml of glacial acetic acid. The mixture is then cooled to 35° C. and subsequently to room temperature, with stirring, after the dropwise addition of 150 ml of water. The precipitated product is isolated by filtration, washed with water and dried at 80° C. in vacuo, affording 27.1 g (99% of theory) of a compound of the formula

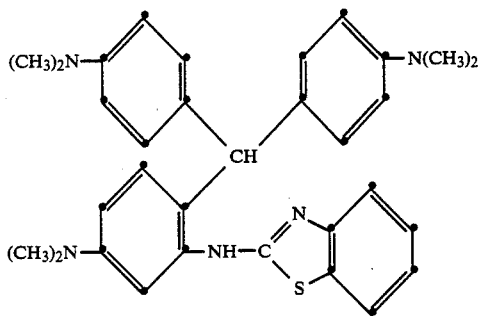

(13)

with a melting point of 167°–168° C.

21.7 g of the above compound are dissolved at 50°–60° C. in 100 ml of dimethylformamide and to this solution are added 9.7 g of chloranil at the same temperature. After stirring for 30 minutes at room temperature, the solution is poured into ice/water and the precipitated product is isolated by filtration and dried at 80° C. in vacuo. The crude product is first chromatographed through a column of alumina with methanol as eluant and subsequently recrystallised from ligroin/toluene. Yield: 4.8 g of the same compound as in Example 1 of the formula (11), which melts at 138°–141° C.

2-Diethylamino-5,5-bis-(4-dimethylaminophenyl)-5,6-dihydroquinazolines of the formula

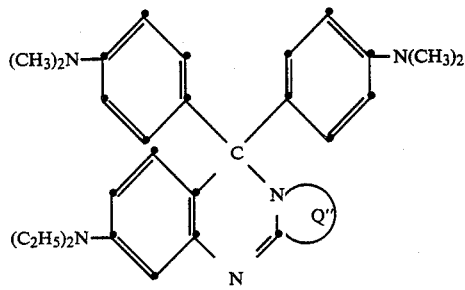

(14)

are prepared in the same manner as in Examples 1 and 2 using the appropriate starting materials.

| Ex. | 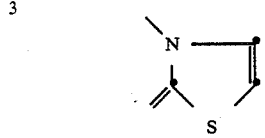 | m.p./°C. | Colour on acid clay |
|---|---|---|---|
| 3 | (N, S ring) | 220–222 | blue |
| 4 | (N, O ring with methyl) | 195–197 | blue |
| 5 | (N, N ring with CH₃, fused benzene) | 234–238 | blue |
| 6 | (N, N ring with OCH₃, OCH₃) | 215–225 (decomp.) | blue |
| 7 | (N, N ring with N(CH₃)₂, N(CH₃)₂) | 218–222 | blue |
| 8 | (N, N ring with H, fused ring with H) | 148–156 (decomp.) | blue |
| 9 | (N, N ring with H, O; fused ring with H, O) | 165–175 (decomp.) | blue |

EXAMPLE 10

Preparation of a pressure-sensitive copying paper

A solution of 3 g of the dihydroquinazoline of the formula (11) obtained in Example 1 in 80 g of diisopropylnaphthalene and 17 g of kerosene are microencapsulated by coacervation in a manner known per se with gelatin and gum arabic. The microcapsules are mixed with starch solution and coated on a sheet of paper. The face of a second sheet of paper is coated with acid-activated bentonite as colour developer. The first sheet and the sheet coated with the developer are laid on top of each other with the coated sides face to face. Pressure is exerted on the first sheet by writing by hand or typewriter and an intense blue copy of excellent lightfastness develops immediately on the sheet coated with the developer.

EXAMPLE 11

1 g of the dihydroquinazoline of the formula (11) is dissolved in 17 g of toluene. With stirring, 12 g of polyvinyl acetate, 8 g of calcium carbonate and 2 g of titanium dioxide are added to this solution. The resultant suspension is diluted with toluene in the weight ratio 1:1 and applied to a sheet of paper with a knife to a thickness of 10 μm. On this sheet of paper is laid a second sheet, the underside of which has been coated to a weight of 3 g/m² with a mixture consisting of 1 part of an amide wax, 1 part of a stearin wax and 1 part of zinc chloride. Pressure is exerted on the top sheet by hand or typewriter and an intense and lightfast blue copy develops immediately on the sheet coated with the colour former.

EXAMPLE 12

Preparation of a heat-sensitive recording material

In a ball mill, 32 g of 4,4′-isopropylidenediphenol (bisphenol A), 3.8 g of the distearylamide of ethylenediamine, 39 g of kaolin, 20 g of an 88% hydrolysed polyvinyl alcohol and 500 ml of water are ground to particle size of about 5 μm. In a second ball mill, 6 g of the dihydroquinazoline of the formula (11), 3 g of a 88% hydrolysed polyvinyl alcohol and 60 ml of water are ground to particle size of about 3 μm.

Both dispersions are mixed and applied to paper to a dry coating weight of 5.5 g/m². An intense blue colour of excellent fastness to light and sublimation is produced by contacting the paper with a heated ball-point pen.

EXAMPLE 13

In a ball mill, 2.7 g of the dihydroquinazoline of the formula (11), 24 g of N-phenyl-N′-(1-hydroxy-2,2,2-trichloroethyl)urea, 16 g of stearylamide, 59 g of an 88% hydrolysed polyvinyl alcohol and 58 ml of water are ground to a particle size of 2–5 μm. This suspension is applied to a sheet of paper to a dry coating weight of 5.5 g/m². An intense and lightfast blue colour is obtained by contacting the paper with a heated ball-point pen.

What is claimed is:

1. A chromgenic dihydroquinazoline of the formula

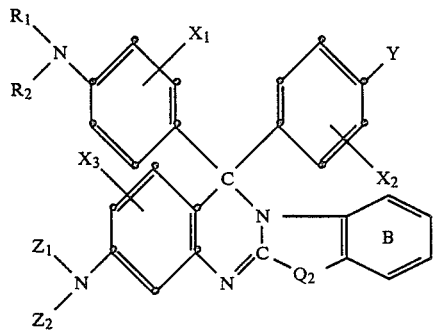

wherein each of $X_1$, $X_2$ and Y independently of one another is hydrogen, halogen, lower alkyl, lower alkanoylamino, $-OR_3$ or $-NR_3R_4$;

$X_3$ is hydrogen, halogen, lower alkyl or lower alkoxy;

each of $R_1$, $R_2$, $R_3$, $R_4$, $Z_1$ and $Z_2$ independently of one another is $C_1-C_{12}$alkyl which is unsubstituted or substituted by halogen, hydroxyl, cyano or lower alkoxy, or is cycloalkyl, phenyl, or phenyl or benzyl each substituted by halogen, nitro, lower alkyl or lower alkoxy, and $R_1$, $R_2$, $R_3$ and $R_4$ are also hydrogen; or each pair of substituents ($R_1$ and $R_2$), ($R_3$ and $R_4$) and ($Z_1$ and $Z_2$) independently of one another, together with the nitrogen atom to which said pair is attached, is a 5- or 6-membered heterocyclic radical;

$Q_2$ is oxygen, sulfur,

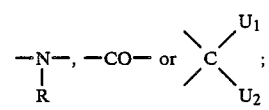

T is hydrogen or lower alkyl; each of $U_1$ and $U_2$ independently of the other is lower alkyl, cyclohexyl, benzyl, or taken together they are alkylene, and the ring B is unsubstituted or substituted by halogen, lower alkyl, lower alkoxy or lower carbalkoxy.

2. A dihydroquinazoline of claim 1, wherein Y is a group of the formula $-NR_3R_4$.

3. A dihydroquinazoline of claim 1, of the formula

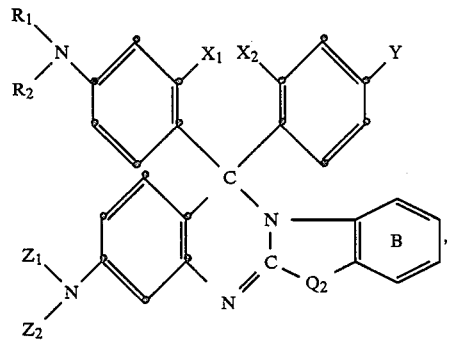

wherein

Y is hydrogen, $-OR_3$ or $-NR_3R_4$; each of $X_1$ and $X_2$ independently of the other is hydrogen, halogen, methyl, methoxy, ethoxy or acetylamino; and each of $R_1$, $R_2$, $R_3$, $R_4$, $Z_1$ and $Z_2$ independently of one another is lower alkyl, cyanoethyl, benzyl or phenyl, or each pair of substituents ($R_1$ and $R_2$), ($R_3$ and $R_4$) and ($Z_1$ and $Z_2$) independently of one another, together with the nitrogen atom to which said pair is attached, is pyrrolidino, piperidino or morpholino.

4. A dihydroquinazoline of claim 3, wherein Y is the group of the formula $-NR_3R_4$.

5. A dihydroquinazoline of claim 4, wherein $R_1=R_2$, $X_1=X_2$, and $Z_1=Z_2$;

each of $Z_1$ and $R_1$ independently of the other is lower alkyl; $X_1$ and $X_2$ are hydrogen, methoxy or ethoxy; and $Q_2$ is $=NT$, $-O-$, $-S-$, $-CO-$, or $=C(CH_3)_2$.

6. A dihydroquinazoline of claim 5, wherein each of $R_1$ and $Z_1$ is methyl or ethyl, $X_1$ is hydrogen, $Q_2$ is sulfur and ring B is unsubstituted.

* * * * *

UNITED STATES PATENT AND TRADEMARK OFFICE
CERTIFICATE OF CORRECTION

PATENT NO. : 4,503,227

DATED : March 5, 1985

INVENTOR(S) : Heinz Balli, Sigmund Gunzenhauser, Ian John Fletcher and Davor Bedekovic It is certified that error appears in the above-identified patent and that said Letters Patent is hereby corrected as shown below:

Claim 1, Column 16, line 20, should read:

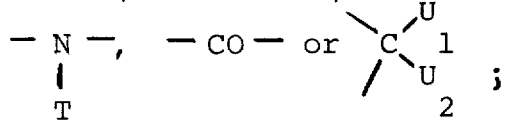

Claim 1, column 15, line 52 should read:

A chromogenic dihydroquinazoline of the formula

Signed and Sealed this

Seventeenth Day of September 1985

[SEAL]

Attest:

Attesting Officer

DONALD J. QUIGG

Commissioner of Patents and Trademarks—Designate